United States Patent
Jia et al.

(10) Patent No.: US 9,662,076 B2
(45) Date of Patent: May 30, 2017

(54) LASER GUIDED AUTO COLLIMATION SYSTEM AND METHOD FOR MEDICAL APPARATUS

(75) Inventors: Lei Jia, Beijing (CN); Lin Lin, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1603 days.

(21) Appl. No.: 13/292,429

(22) Filed: Nov. 9, 2011

(65) Prior Publication Data

US 2012/0116374 A1 May 10, 2012

(30) Foreign Application Priority Data

Nov. 9, 2010 (CN) .......................... 2010 1 0552002

(51) Int. Cl.
  *A61B 6/08* (2006.01)
  *A61B 6/04* (2006.01)

(52) U.S. Cl.
  CPC .............. *A61B 6/0492* (2013.01); *A61B 6/08* (2013.01)

(58) Field of Classification Search
  CPC ......... A61B 6/0492; A61B 6/08; A61B 6/587; A61B 6/547; A61B 6/4405; A61B 6/4441; A61B 6/583; A61B 6/04; A61B 6/4283; A61B 6/588; A61B 90/39; A61B 6/145; A61B 6/4233; A61B 6/4291; A61B 6/467; A61B 2090/376; A61B 6/032;
  (Continued)

(56) References Cited

U.S. PATENT DOCUMENTS 5,588,430 A   12/1996   Bova et al.
5,590,665 A   1/1997    Kanai
              (Continued)

FOREIGN PATENT DOCUMENTS

CN   1244782 A   2/2000
CN   1933782 A   3/2007
          (Continued)

OTHER PUBLICATIONS http://en.wikipedia.org/wiki/Pinhole_camera_model (5 pages).
(Continued)

*Primary Examiner* — Irakli Kiknadze
(74) *Attorney, Agent, or Firm* — GE Global Patent Operation; Marc A. Vivenzio

(57) ABSTRACT

A collimation system for a medical apparatus includes a collimation component having a laser emitting device, at least one photographing device, and a computing device. The laser emitting device is configured to the emit a laser beam to irradiate on a landmark on a body surface of a patient, the at least one photographing device is configured to take a photograph of a laser irradiation spot, and the computing device is configured to obtain a position of the laser irradiation spot by performing computation on images obtained by the at least one photographing device. The system further includes a moving component provided on the medical apparatus and configured to move to a target position for performing diagnosis or treatment. The medical apparatus automatically is configured to locate the moving component based on the position of the irradiation spot obtained from the computation.

16 Claims, 5 Drawing Sheets

(58) Field of Classification Search
CPC ....... A61B 6/0457; A61B 18/20; A61B 18/22; A61B 2018/00452; A61B 18/203; A61B 18/1815; A61B 18/18; A61B 18/24; A61B 18/14; A61B 2018/00791; A61B 2018/0016; A61B 2018/00702; A61B 2018/00291; A61B 2018/00577; A61B 2018/00601; A61B 5/0077; A61B 5/0075; A61B 5/445; A61B 5/0059; A61B 5/02416; A61B 5/7278; A61B 5/0071; A61B 5/01; A61B 5/0261; A61B 5/14551; A61B 5/489; A61B 5/6898; A61B 5/7425
USPC ....... 378/4, 17, 20, 145, 163, 166, 205, 206; 606/13
See application file for complete search history.

(56) References Cited

U.S. PATENT DOCUMENTS

| | | | |
|---|---|---|---|
| 5,598,269 | A | 1/1997 | Kitaevich et al. |
| 5,823,192 | A | 10/1998 | Kalend et al. |
| 6,272,368 | B1 | 8/2001 | Alexandrescu |
| 7,478,949 | B2 | 1/2009 | Niessen et al. |
| 7,928,410 | B2* | 4/2011 | Ose ...................... A61N 5/1049 250/491.1 |
| 2002/0118280 | A1 | 8/2002 | Medlar et al. |
| 2003/0185349 | A1* | 10/2003 | Roeckseisen ............ A61B 6/08 378/206 |
| 2008/0063400 | A1* | 3/2008 | Hudson .................. A63H 30/04 398/106 |
| 2008/0287728 | A1 | 11/2008 | Mostafavi et al. |
| 2009/0190722 | A1* | 7/2009 | Windt ...................... A61B 6/08 378/206 |
| 2009/0220415 | A1* | 9/2009 | Shachaf ............... A61B 5/0071 424/1.11 |

FOREIGN PATENT DOCUMENTS

| | | |
|---|---|---|
| CN | 101537230 A | 9/2009 |
| JP | 08126638 A | 5/1996 |
| JP | 08257024 A | 10/1996 |
| JP | 2000262511 A | 9/2000 |
| JP | 2006277085 A | 10/2006 |

OTHER PUBLICATIONS

Unofficial English Translation of Chinese Office Action issued in connection with corresponding CN Application No. 201010552002.3 on Jun. 13, 2014.

Unofficial English Translation of Japanese Office Action issued in connection with corresponding JP Application No. 2011225406 on Aug. 4, 2015.

* cited by examiner

LASER GUIDED AUTO COLLIMATION SYSTEM AND METHOD FOR MEDICAL APPARATUS

CROSS REFERENCE TO RELATED APPLICATIONS

This application claims the benefit of Chinese Patent Application No. 201010552002.3 filed Nov. 9, 2010, which is hereby incorporated by reference in its entirety.

BACKGROUND OF THE INVENTION

The present application relates to the field of medical apparatus including medical imaging apparatus and treatment system, particularly to an X-ray apparatus and system; and relates to the collimation of the position of the body of a patient through collimation of an irradiation landmark on the body surface of the patient.

Radiography usually requires precise collimation of a particular position on the body surface of a patient. Precise and fast collimation is the key point of successful irradiation and helps to reduce the time of the whole irradiation process and to decrease patient discomfort.

Currently, the procedure of collimating a patient of a digital radiography system with automatic collimation function (such as a GE Definium 8000 system, see FIG. 1) generally includes the following steps: (i) selecting a patient; (ii) selecting an initial position for the overhead tube suspension (OTS) (as shown in the dropdown menu A); (iii) pressing and holding the automatic collimation button B (see the control panel), the OTS starting to move towards a target position, releasing the button when the OTS moves to the target position; (iv) instructing the patient to the specific position (before the chest-radiography stand, on the bed or other position); (v) manually moving and/or rotating the tube to collimate at the irradiation landmark on the body surface of the patient and re-confirming the field of view (FOV) of the irradiation and so on. When confirming the FOV, the central ray should be collimated at the irradiation landmark on the body surface of the patient. For example, as shown in FIG. 2, for a lying position, the central ray (5) emitted by the tube (8) is usually perpendicular to the patient and at a particular position directly over the irradiation landmark (3) on the body surface, the irradiation landmark (3) on the body surface is located at the center of the FOV (4) of irradiation.

From this it can be seen that this type of system cannot realize completely automatic collimation of a patient. Wherein, although the OTS moves towards a target position automatically, the collimation of the movement and/or rotation of the tube is manually performed. Precise collimation of an irradiation landmark on the body surface of a patient by using this method takes a long time and the work flow is rather complicated.

U.S. Pat. No. 5,590,665 discloses a laser guided lesion localization apparatus, but the apparatus does not perform collimation at an irradiation landmark on the body surface of a patient. Another U.S. Pat. No. 5,598,269 discloses a movable laser guided alignment apparatus for assisting a CT apparatus in collimation, which includes two beam sources of a laser line beam source and a laser fan beam source. However, the apparatus is complex in structure and inconvenient in operation.

SUMMARY OF THE INVENTION

The embodiments described herein provide a laser guided automatic collimation system and method for medical apparatus for performing precise collimation of an irradiation landmark on the body surface of a patient.

Further, the embodiments described herein provide a collimation system for a medical apparatus, including a medical apparatus itself and a collimation component, wherein a moving component is provided on the medical apparatus and which can move to a target position for performing diagnosis or treatment. The collimation component includes a laser emitting device, a photographing device, and a computing device. The laser beam emitted by the laser emitting device irradiates on a landmark on the body surface of a patient. The photographing device takes photographs of the laser irradiation spot. The computing device obtains a position of the laser irradiation spot by performing computation on images obtained by the photographing device. The medical apparatus automatically locates the moving component based on the position of the irradiation spot obtained from the computation.

Preferably, the laser emitting device is hand-held.

A controller is provided on the laser emitting device for controlling continuous emission of laser pulses.

Once the controller on the laser emitting device starts to continuously emit laser pulses, the controller triggers the photographing device to start taking photographs. The acquisition frequency of the photographing device is higher than the emission frequency of the laser pulses.

Preferably, the acquisition frequency of the photographing device is twice of the frequency of laser pulses.

The computing device does subtraction computation to adjacent images acquired by the photographing device to obtain a position of the laser irradiation spot.

When the positions of the laser irradiation spot obtained by the computing device remain consistent for a period of time, the laser emitting device stops to emit laser pulses.

The remaining consistent for a period of time means that the difference between the positions of the laser irradiation spot obtained by the computing device for multiple times is smaller than a predetermined threshold value.

At least three photographing devices are arranged in the surrounding of the environment where the medical apparatus is placed.

Preferably, the medical apparatus is an X-ray diagnosis apparatus, and the photographing device is a digital camera.

The embodiments described herein provide a collimation method for a medical apparatus. The method includes: 1) emitting a laser beam to irradiate on a landmark on the body surface of a patient; 2) taking photographs of the laser irradiation spot; 3) computing the images obtained from the photographing to obtain a position of the laser irradiation spot; and 4) automatically locating a moving component based on the position of the irradiation spot obtained from the computation.

Preferably, in step 1), a hand-held laser emitting device is used for laser emission.

Step 1) further includes starting to emit laser pulses continuously and triggering the photographing device to start taking photographs once laser pulses start to be emitted continuously.

In step 2), the acquisition frequency of photographing the laser irradiation spot is higher than the emission frequency of the laser pulses.

Preferably, in step 2), the acquisition frequency of photographing the laser irradiation spot is twice of the frequency of laser pulses.

In step 3), subtraction computation is performed on adjacent images obtained in the photographing to obtain a position of the laser irradiation spot.

In step 3), when the positions of the laser irradiation spot obtained from computation remain consistent for a period of time, step 1) terminates, i.e. stopping to emit laser pulses.

In step 3), the remaining consistent for a period of time means that the difference between the positions of the laser irradiation spot obtained by the computing device for multiple times over a predetermined period of time is smaller than a predetermined threshold value.

At least three photographing devices are arranged to take photographs of the laser irradiation spot.

Preferably, the medical apparatus is an X-ray diagnosis apparatus, and the photographing device is a digital camera.

The embodiments described herein simplify the work flow of automatic collimation for a medical apparatus, provide automatic collimation and help to improve patient experience.

DETAILED DESCRIPTION OF THE INVENTION

The present invention is described in detail by way of specific embodiments, but the present invention is not merely limited to this.

Below the specific embodiments are described in detail in conjunction with the drawings, these embodiments are not intended to limit the present invention. In the following text, the same reference number is used for the same component part in different figures.

Figure 1:
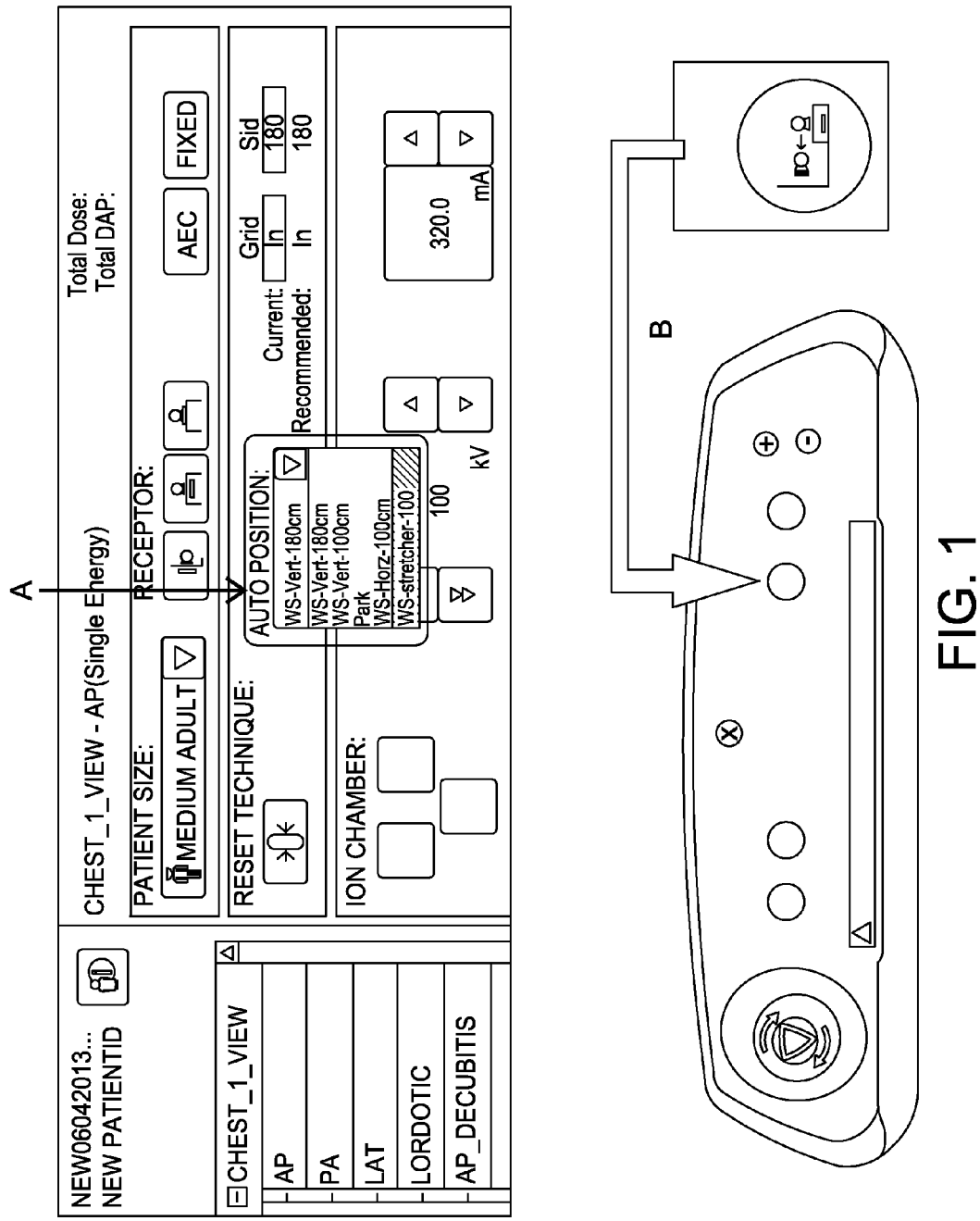
FIG. 1 shows a user operation interface and related buttons of a GE Definium 8000 system, which is a digital ray system having an automatic collimation function.
Figure 2:
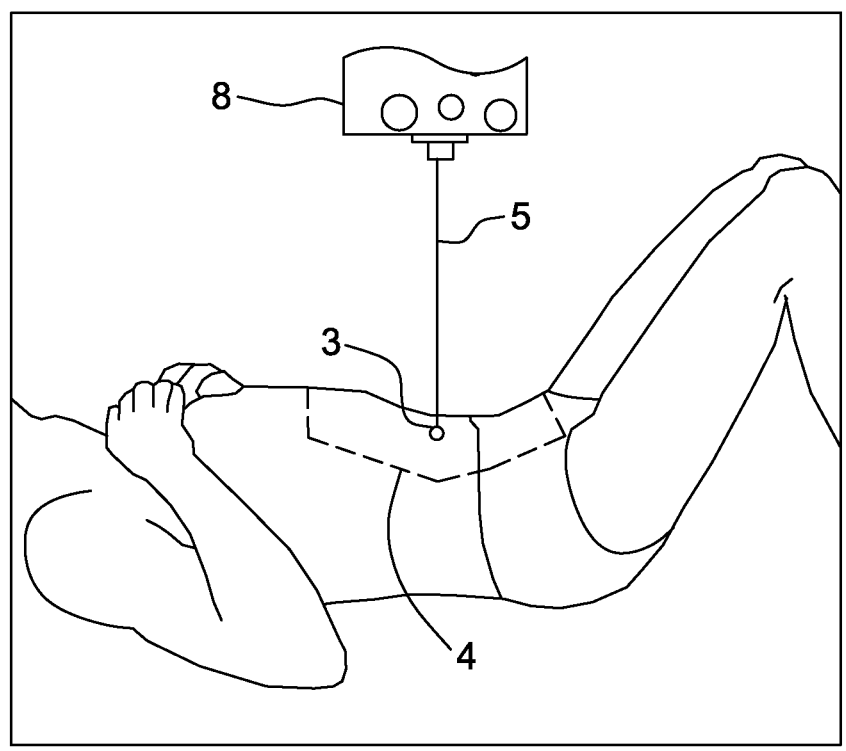
FIG. 2 shows a schematic diagram of a medical apparatus performing collimation on a patient in a lying position.
Figure 3:
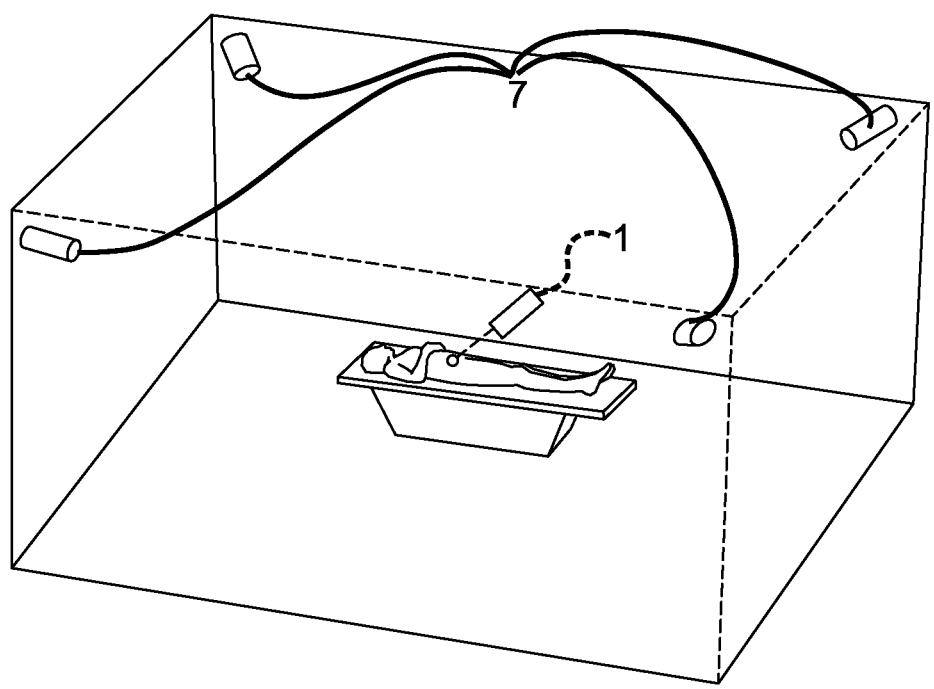
FIG. 3 shows a structural diagram of an exemplary embodiment of a collimation system for a medical apparatus.
Figure 4:
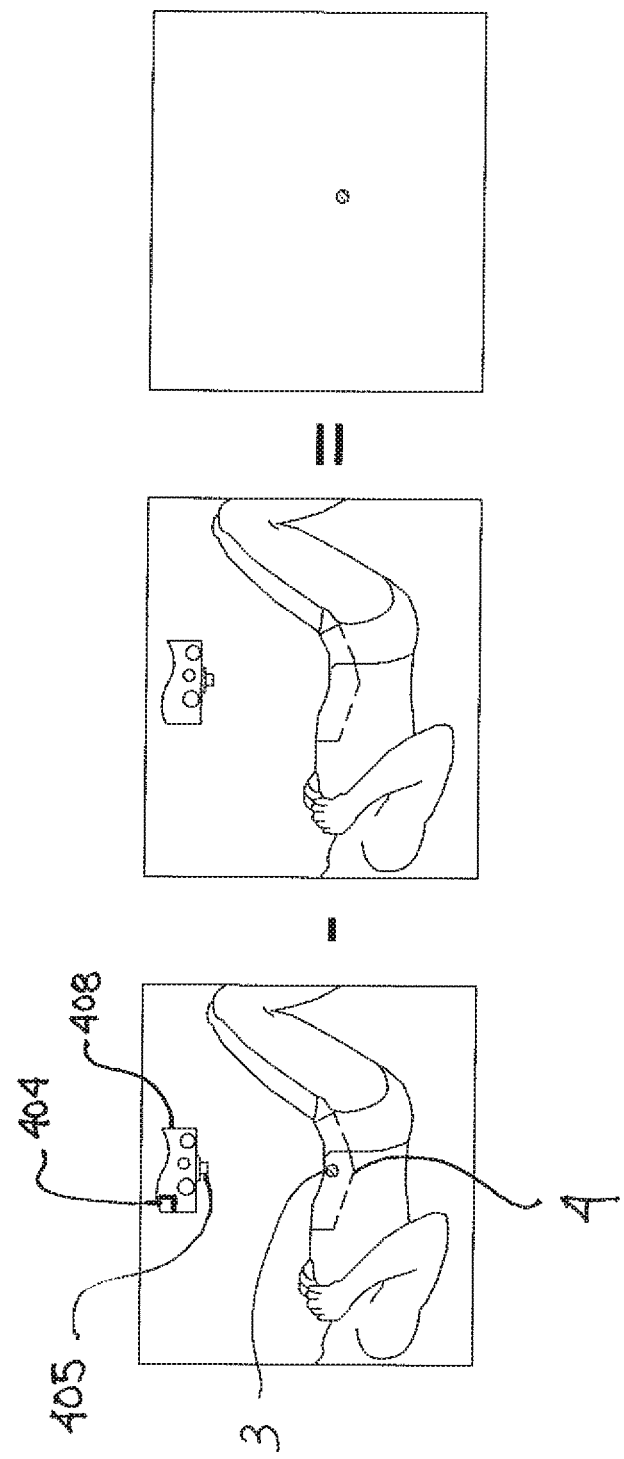
FIG. 4 is a schematic diagram of performing computation on adjacent images obtained through photographing to obtain a position of a laser irradiation spot.

A preferred embodiment is a collimation system for a medical apparatus, particularly such as an X-ray diagnosis apparatus, as shown in FIGS. 3 and 4. Wherein, an exemplary medical apparatus 408, (i.e. the X-ray diagnosis apparatus) is shown in FIG. 4. A laser emitting device in the collimation component is a hand-held laser pulse emission pen (1) with a button thereon for controlling emission of laser pulses. An operator holds the laser pulse emission pen, presses the button to continuously emit laser pulses and directs the laser pulses toward an irradiation landmark on the body surface of a patient. The collimation component further comprises a plurality of digital cameras. FIG. 3 shows four digital cameras (7) arranged at the four wall corners in the ceiling of the irradiation room facing the center of the irradiation room or the location of the patient. Once the laser pen emits laser pulses, all the cameras are triggered to start taking photographs. The photographing frequency is higher than the emission frequency of the laser pulses. The acquisition frequency of said cameras is preferably twice of the frequency of the laser pulses such that an image is acquired at each of the two phases of peak and valley of the laser pulses respectively. Since a camera is arranged in each of the four directions, the laser irradiation spot is necessarily photographed by one or even more of the cameras. Wherein, the digital cameras transmit the obtained images of the laser irradiation spot to a computing device 404 on the medical apparatus 408. The computing device 404 does subtraction computation on the adjacent two images obtained by the cameras continuously, as shown in FIG. 4, so as to obtain the position of the laser irradiation spot continuously (the algorithm for converting the images of the irradiation spot obtained by the cameras into coordinates of the position of the irradiation spot can be seen in the following text). From the moment a position of the laser irradiation spot is first obtained, the computing device 404 computes the variations of the position of the irradiation simultaneously and continuously. When it is found that the position of the irradiation spot remains consistent for a period of time, for example, if the difference between any two computed positions of the laser irradiation spot within one second is smaller than a predetermined threshold value, the system beeps to remind the operator to release the laser emission button so as to stop laser emission and collimation operation.

A preferred algorithm of projecting perspective images obtained by the cameras to a three-dimensional (3D) coordinate point on an image plane is a pinhole camera model. Assuming that the coordinates of the position of a laser irradiation spot to be determined is (X0, Y0, Z0), then computation of Z0 is unnecessary because the X-ray source to image-receptor distance (SID) is preset by the system (based on the irradiation part). The system only needs to compute the planar coordinates (X0, Y0) of the central ray on the irradiation plane.

The equation used in the algorithm is as follows:

$$sm' = A[R \mid t]M'$$

Or $$s \begin{bmatrix} u \\ v \\ 1 \end{bmatrix} = \begin{bmatrix} f_x & 0 & c_x \\ 0 & f_y & c_y \\ 0 & 0 & 1 \end{bmatrix} \begin{bmatrix} r_{11} & r_{12} & r_{13} & t_1 \\ r_{21} & r_{22} & r_{23} & t_2 \\ r_{31} & r_{32} & r_{33} & t_3 \end{bmatrix} \begin{bmatrix} X \\ Y \\ Z \\ 1 \end{bmatrix}$$

Wherein (X, Y, Z) represents a three-dimensional coordinate of one point within irradiation room coordinate space, (u, v) represents pixel coordinates of projection points. A is referred to as the matrix of cameras or the matrix of intrinsic parameters: wherein ($c_x$, $c_y$) is the coordinate of the core point (generally the center of the image); $f_x$, $f_y$ represent lengths of the focal distances in pixels. According to this equation, if an image is scaled at a certain parameter, all parameters should be scaled accordingly (multiplied or divided by the parameter). The matrix of intrinsic parameters do not vary with the changes of the Field of View of cameras, once the matrix of intrinsic parameters is determined, it can be used repeatedly (if only the focal distance is kept the same). The joint rotation-translation matrix [R|t] is called as a matrix of extrinsic parameters, and used to describe the rotation motion of the camera around some point, a still camera, or the turning motion of an object in front of the camera. Then the [R|t] can project the coordinates of some point (X, Y, Z) on the image onto some coordinate system according to the camera. The transformed mathematic formula is (when Z≠0):

$$\begin{bmatrix} x \\ y \\ z \end{bmatrix} = R \begin{bmatrix} X \\ Y \\ Z \end{bmatrix} + t$$

$$x' = x/z$$

$$y' = y/z$$

$$u = f_x * x' + c_x$$

$$v = f_y * y' + c_y$$

Thus, the position (X0, Y0) of the target spot of the laser irradiation spot can be obtained by performing the aforesaid computation on the images acquired by different cameras at the same moment.

Figure 5:
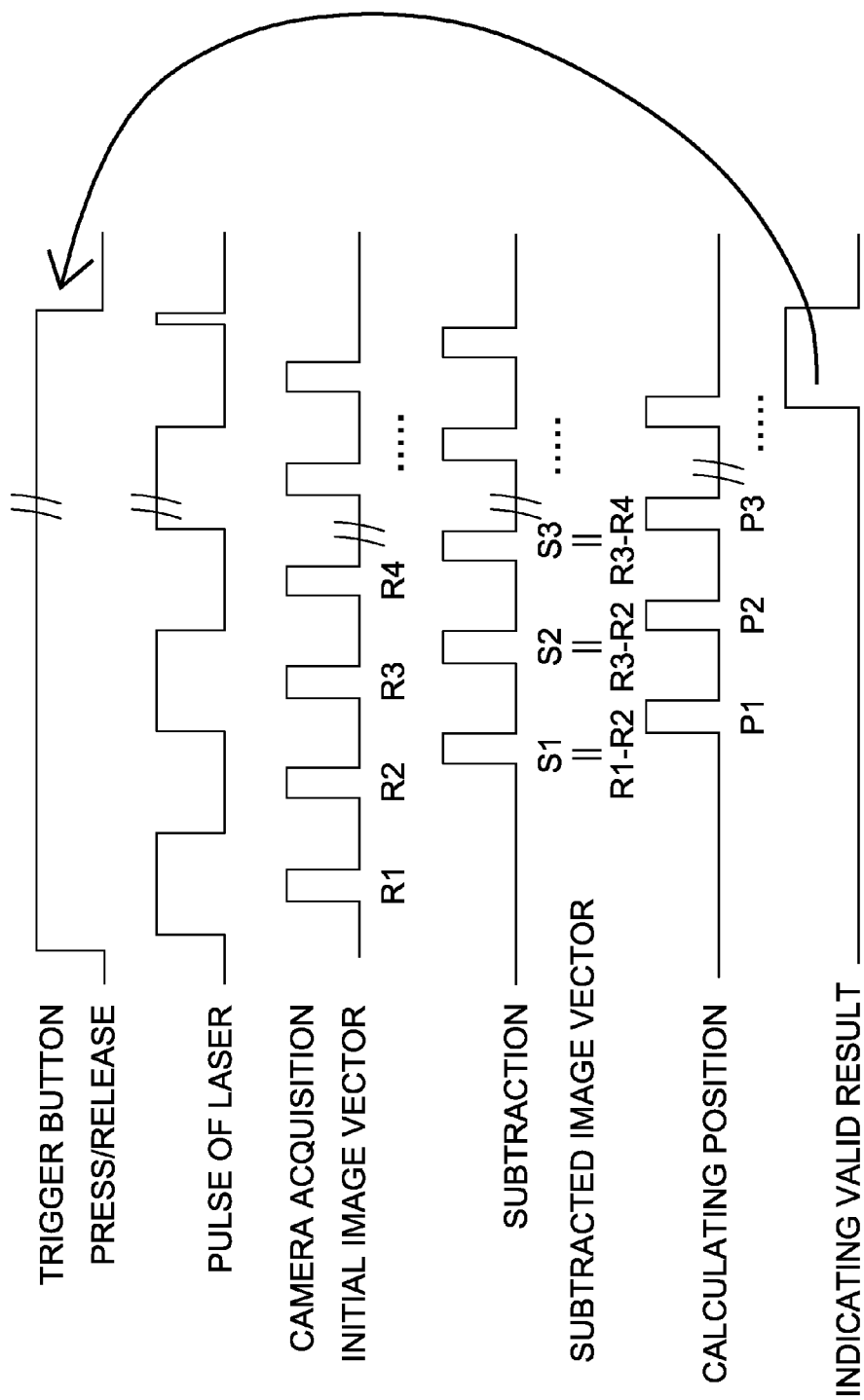
FIG. 5 shows a control timing chart of an exemplary collimation method for a medical apparatus.

Another preferred embodiment includes a collimation method for medical apparatus as shown in the control timing chart in FIG. 5, particularly a collimation method for an X-ray diagnosis apparatus. The method includes the following steps.

1) An operator uses a hand-held laser pulse emission pen, presses and holds the laser emission button to emit laser pulses continuously, and directs the laser beam toward an irradiation landmark on the body surface of a patient.

2) A plurality of digital cameras are arranged in the surrounding of the X-ray irradiation room for taking photographs of the patient. For example, at least three digital cameras are arranged surrounding the X-ray irradiation room. Once the laser emission button on the laser emission pen is pressed, laser pulses start to be emitted continuously. The laser pulses trigger the cameras to take photographs of the laser irradiation spot. The acquisition frequency of photographs is higher than the emission frequency of the laser pulses. Preferably, the acquisition frequency of taking photographs of the laser irradiation spot is twice the laser pulse frequency such that an image is acquired at each of the two phases of peak and valley of the laser pulses respectively.

3) Subtraction computation is performed to adjacent images acquired in the photographing continuously to obtain positions of the laser irradiation spot continuously.

4) Since the cameras start to obtain an initial image vector of the laser irradiation spot, the existing algorithm (shown above) can be applied to convert position images of the irradiation spot obtained by the cameras to position coordinates (vector) of the irradiation spot.

5) In the meanwhile, distance between the obtained positions of the irradiation spot is computed continuously.

6) When it is found that the position of the irradiation spot remains consistent for a period of time. For example, if the difference between any two obtained positions of the laser irradiation spot within one second is smaller than a predetermined threshold value or the obtained positions are completely identical, the system beeps to indicate that a position of the landmark on the body surface of the patient has been obtained and to remind the operator to release the laser emission button to stop laser emission and collimation operation.

7) The X-ray diagnosis apparatus guides the OTS and/or tube 405 of the medical apparatus 408, also referred to as the moving component 405, to collimate automatically, i.e. automatically moving to an appropriate position for irradiating the landmark 403 on the body surface 404 of the patient, in accordance with the obtained position of the landmark on the body surface of the patient.

The collimation system and method for medical apparatus described herein can be applied to a diagnosis or treatment apparatus that requires precise collimation. Apart from an X-ray system, the collimation system and method can be further applied to a computed tomography (CT) apparatus, a magnetic resonance (MR) apparatus and a positron emission tomography (PET) apparatus and so on.

What are described above are only an illustrative description of the present invention, and are not used to limit the scope of protection of the present invention. It should be understood that those skilled in the art can make improvements, modifications or variations to the present invention. However, such improvements, modifications or variations are considered to fall within the scope of protection of the present application without departing from the spirit of the present invention.

What is claimed is:

1. A collimation system for a medical apparatus, said collimation system comprising:
    a collimation component comprising a laser emitting device, at least one photographing device, and a computing device, wherein the laser emitting device is configured to the emit a laser beam to irradiate a landmark on a body surface of a patient, the at least one photographing device is configured to take a photograph of a laser irradiation spot, and the computing device is configured to obtain a target position of the laser irradiation spot by performing computation on images obtained by the at least one photographing device; and
    a moving component provided on the medical apparatus the moving component configured to be positioned and move to the target position for performing diagnosis or treatment, wherein the medical apparatus automatically is configured to locate the target position based on the position of the irradiation spot obtained from the computation, wherein said laser emitting device comprises a controller configured to control continuous emission of laser pulses and the controller is configured to trigger the at least one photographing device to start taking photographs once the controller starts to continuously emit laser pulses, wherein an acquisition frequency of the at least one photographing device is higher than an emission frequency of the laser pulses.

2. The collimation system according to claim 1, wherein said laser emitting device comprises a hand-held device.

3. The collimation system according to claim 1, wherein the acquisition frequency of the at least one photographing device is twice the frequency of the laser pulses.

4. The collimation system according to claim 1, wherein the computing device is configured to perform a subtraction computation on adjacent images obtained by the at least one photographing device to obtain a position of the laser irradiation spot.

5. The collimation system according to claim 4, wherein the laser emitting device is configured to stop emitting laser pulses when the position of the laser irradiation spot obtained by the computing device remains consistent for a period of time.

6. The collimation system according to claim 5, wherein a difference between positions of the laser irradiation spot obtained by the computing device for multiple times is smaller than a predetermined threshold value when the position remains consistent.

7. The collimation system according to claim 1, wherein the least one photographing device comprises at least three photographing devices arranged to surround the medical apparatus.

8. The collimation system according to claim 7, wherein said medical apparatus comprises an X-ray diagnosis apparatus, and said at least one photographing device comprises at least one digital camera.

9. A collimation method for a medical apparatus, said method comprising
- emitting a laser beam to irradiate on a landmark on a body surface of a patient by continuously emitting laser pulses from a laser emitting device;
- controlling a trigger of cameras to start taking photographs when the laser pulses begin to be emitted continuously;
- taking photographs of a laser irradiation spot at an acquisition frequency that is higher than an emission frequency of the laser pulses;
- obtaining a position of the laser irradiation spot by computing images obtained from the photographing; and
- automatically locating and positioning a moving component based on the position of the laser irradiation spot obtained from the computation.

10. The collimation method according to claim 9, wherein emitting a laser beam further comprises emitting the laser beam using a hand-held laser emitting device.

11. The collimation method according to claim 10, wherein acquiring photographs of the laser irradiation spot at an acquisition frequency further comprises acquiring photographs of the laser irradiation spot at an acquisition frequency that is twice the frequency of the laser pulses.

12. The collimation method according to claim 10, wherein obtaining a position further comprises performing subtraction computation on adjacent images obtained from the photographing to obtain the position of the laser irradiation spot.

13. The collimation method according to claim 12, further comprises terminating emission of the laser pulses when the position of the laser irradiation spot obtained from the computation remains consistent for a period of time.

14. The collimation method according to claim 13, wherein terminating emission of the laser pulses further comprises terminating emissions of the laser pulses when a difference between positions of the laser irradiation spot obtained by the computing device for multiple times over a predetermined period of time is smaller than a predetermined threshold value.

15. The collimation method according to claim 10, further comprises arranging at least three photographing devices to take photographs of the laser irradiation spot.

16. The collimation method according to claim 15, wherein the medical apparatus is an X-ray diagnosis apparatus, and each photographing device is a digital camera.

* * * * *